US009770584B2

(12) United States Patent
Thakur et al.

(10) Patent No.: US 9,770,584 B2
(45) Date of Patent: Sep. 26, 2017

(54) SYSTEM AND METHODS FOR TREATING ATRIAL FIBRILLATION USING HEMODYNAMIC RESPONSES

(71) Applicant: Cardiac Pacemakers, Inc., St. Paul, MN (US)

(72) Inventors: Pramodsingh Hirasingh Thakur, Woodbury, MN (US); Ramesh Wariar, Blaine, MN (US); Barun Maskara, Blaine, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/699,527

(22) Filed: Apr. 29, 2015

(65) Prior Publication Data

US 2015/0343223 A1 Dec. 3, 2015

Related U.S. Application Data

(60) Provisional application No. 62/004,595, filed on May 29, 2014.

(51) Int. Cl.
*A61N 1/00* (2006.01)
*A61N 1/05* (2006.01)
(Continued)

(52) U.S. Cl.
CPC .......... *A61N 1/056* (2013.01); *A61B 5/02028* (2013.01); *A61B 5/046* (2013.01);
(Continued)

(58) Field of Classification Search
CPC .................................. A61B 5/02; A61N 1/056
(Continued)

(56) References Cited

U.S. PATENT DOCUMENTS 7,336,994 B2  2/2008  Hettrick et al.
8,509,895 B2  8/2013  Rom
(Continued)

FOREIGN PATENT DOCUMENTS

WO   WO-2004096351 A1   11/2004
WO   WO-2015183458 A1   12/2015

OTHER PUBLICATIONS

"International Application Serial No. PCT/US2015/028228, International Search Report mailed Aug. 31, 2015", 3 pgs.
(Continued)

*Primary Examiner* — Nadia A Mahmood
(74) *Attorney, Agent, or Firm* — Schwegman Lundberg & Woessner, P.A.

(57) ABSTRACT

Systems and methods for treating atrial tachyarrhythmias such as atrial fibrillation (AF) are disclosed. By monitoring a patient's hemodynamic sensor response to a candidate AF therapy, the present systems and methods can be used to determine an individualized AF therapy leading to a desirable hemodynamic outcome. A medical system can include one or more programmable therapy circuits and a hemodynamic sensor circuit. The system includes a therapy selection circuit that automatically programs and sequentially delivers at least a first candidate therapy and a different second candidate therapy. By comparing the values of a hemodynamic parameter in response to or during the first candidate therapy to that in response to or during the second candidate therapy, a desired AF therapy can be determined as the candidate therapy that leads to faster or more significant hemodynamic recovery.

20 Claims, 6 Drawing Sheets

(51) Int. Cl.
    *A61B 18/12* (2006.01)
    *A61M 5/172* (2006.01)
    *A61N 1/362* (2006.01)
    *A61N 1/365* (2006.01)
    *A61N 1/368* (2006.01)
    *A61N 1/39* (2006.01)
    *A61B 5/02* (2006.01)
    *A61B 5/046* (2006.01)
    *A61B 18/00* (2006.01)
    *A61B 5/021* (2006.01)
    *A61B 5/024* (2006.01)
    *A61B 5/029* (2006.01)
    *A61B 5/11* (2006.01)

(52) U.S. Cl.
    CPC ....... *A61B 18/1206* (2013.01); *A61M 5/1723* (2013.01); *A61N 1/368* (2013.01); *A61N 1/3624* (2013.01); *A61N 1/36578* (2013.01); *A61N 1/36585* (2013.01); *A61N 1/395* (2013.01); *A61B 5/021* (2013.01); *A61B 5/029* (2013.01); *A61B 5/02405* (2013.01); *A61B 5/1118* (2013.01); *A61B 2018/00577* (2013.01); *A61B 2018/00642* (2013.01); *A61B 2018/00839* (2013.01); *A61M 2005/1726* (2013.01)

(58) Field of Classification Search
    USPC ...................................... 607/17, 18
    See application file for complete search history.

(56) References Cited

U.S. PATENT DOCUMENTS

| | | |
|---|---|---|
| 2006/0069322 A1 | 3/2006 | Zhang et al. |
| 2006/0095083 A1 | 5/2006 | Zhang et al. |
| 2006/0116593 A1 | 6/2006 | Zhang et al. |
| 2006/0253043 A1 | 11/2006 | Zhang et al. |
| 2006/0253044 A1 | 11/2006 | Zhang et al. |
| 2006/0253162 A1 | 11/2006 | Zhang et al. |
| 2006/0253164 A1 | 11/2006 | Zhang et al. |
| 2007/0142733 A1 | 6/2007 | Hatlestad et al. |
| 2007/0167849 A1 | 7/2007 | Zhang et al. |
| 2009/0076557 A1 | 3/2009 | Zhang et al. |
| 2009/0131999 A1 | 5/2009 | Li |
| 2010/0023078 A1 | 1/2010 | Dong et al. |
| 2010/0298729 A1 | 11/2010 | Zhang et al. |
| 2011/0137192 A1 | 6/2011 | Zhang et al. |
| 2011/0144511 A1 | 6/2011 | Zhang et al. |
| 2012/0165890 A1 | 6/2012 | Min |
| 2012/0221066 A1 | 8/2012 | Rosenberg et al. |
| 2012/0221069 A1 | 8/2012 | Rosenberg et al. |
| 2012/0226328 A1 | 9/2012 | Dong et al. |
| 2012/0245475 A1 | 9/2012 | Hatlestad et al. |
| 2012/0289847 A1 | 11/2012 | Zhang et al. |
| 2012/0296228 A1* | 11/2012 | Zhang ................. A61B 5/0006 600/513 |
| 2012/0330171 A1 | 12/2012 | Zhang et al. |
| 2013/0165802 A1 | 6/2013 | Dalal et al. |
| 2013/0184545 A1 | 7/2013 | Blomqvist et al. |
| 2013/0204312 A1 | 8/2013 | Gill et al. |
| 2013/0211472 A1* | 8/2013 | Blomqvist ........... A61N 1/3627 607/18 |
| 2013/0325083 A1 | 12/2013 | Bharmi et al. |

OTHER PUBLICATIONS

"International Application Serial No. PCT/US2015/028228, Written Opinion mailed Aug. 31, 2015", 5 pgs.

Naqvi, Tasneem Z., et al., "Method of Atroventricular Programming in Atrial Flutter in Patients with Biventricular Pacemaker", PACE, vol. 30, (Aug. 2007), 948-956.

Waggoner, Alan D., et al., "Improvements in Left Ventricular Diastolic: Function After Cardiac Resynchronization Therapy Are Coupled to Response in Systolic Performance", JAAC; vol. 46, No. 12. (Dec. 20, 2005), 2244-2249.

* cited by examiner

SYSTEM AND METHODS FOR TREATING ATRIAL FIBRILLATION USING HEMODYNAMIC RESPONSES

CLAIM OF PRIORITY

This application claims the benefit of priority under 35 U.S.C. §119(e) of U.S. Provisional Patent Application Ser. No. 62/004,595, filed on May 29, 2014, which is herein incorporated by reference in its entirety.

TECHNICAL FIELD

This document relates generally to medical devices, and more particularly, to systems, devices and methods for determining a desirable therapy for treating atrial tachyarrhythmia based on hemodynamic responses.

BACKGROUND

Atrial fibrillation (AF) is the most common clinical arrhythmia, and accounts for approximately one third of admissions resulting from cardiac rhythm disturbances. An estimated 2.3 million people in North America have AF. During AF, the normal regular sinus rhythm is overwhelmed by disorganized electrical pulses originated from regions in or near an atrium. This can lead to irregular conductions to ventricles, thereby causing inappropriately fast and irregular heart rate. One type of AF is paroxysmal AF which may last from minutes to days before it stops by itself. Another type known as persistent AF may last for over a week and typically requires medication or other treatment to revert to normal sinus rhythm. The third type, permanent AF, is a condition where a normal heart rhythm cannot be restored with treatment. Persistent AF can become more frequent and result in permanent AF.

Congestive heart failure (CHF) is another major cardiovascular epidemic and affects over five million people in the United States alone. CHF is the loss of pumping power of the heart, resulting in the inability to deliver enough blood to meet the demands of peripheral tissues. CHF patients typically have enlarged heart with weakened cardiac muscles, resulting in reduced contractility and poor cardiac output of blood. CHF can affect the left heart, right heart or both sides of the heart, resulting in non-simultaneous contractions of the left ventricle and contractions of the right ventricle. Such non-simultaneous contractions, also known as dyssynchroncy between the left and right ventricles, can further decrease the pumping efficiency of the heart.

There is a close pathophysiological relationship between AF and CHF. A large percentage of CHF patients may experience AF or other types of atrial tachyarrhythmias. AF may facilitate the development or progression of CHF, and CHF can increase the risk for the development of AF. The prevalence of AF in patients with CHF increased in parallel with the severity of CHF.

Atrial tachyarrhythmias, such as AF, can coexist with HF in many CHF patients. AF may facilitate the development or progression of CHF in several ways. For example, during AF, irregularity of the ventricular contractions can result in reduction in left ventricular (LV) filling during short cycles which is not completely compensated for by increased filling during longer cycles. The loss of effective atrial contractile function also contributes to the deterioration of LV filling, particularly in CHF patients with diastolic dysfunction. Presence of untreated or uncontrolled AF may also reduce effectiveness of CHF therapies.

Timely treatment of AF is important in preventing the exacerbating effect of AF on CHF patients. It can also prevent thrombus formation and therefore reduce risk of stroke. Patients with AF frequently experience inappropriately rapid heart rate and irregular ventricular rhythm due to the loss of normal AV synchrony. Based on such characteristic clinical manifestation, AF can be detected from cardiac electrophysiological signals such as electrocardiogram (ECG) or intracardiac electrogram (EGM). Therapy options for treating an AF episode can include pharmacological therapy such as antiarrhythmic drugs, surgical therapy such as catheter ablation, or electrical stimulation therapy such as provided by a bedside or ambulatory electrostimulator such as an implantable medical device (IMD).

Depending on the objectives of AF management, there are two types of AF therapies, namely rate control therapies and rhythm control therapies. The goal of the rate control is to reduce and regularize the ventricular contractions without necessarily correcting the ongoing AF rhythm, so as to achieve improvement in hemodynamic status. The goal of the rhythm control is to correct the AF rhythm, restore and maintain a normal sinus rhythm (NSR). Different types, duration, or other characteristics of AF episodes, and a patient's health status and underlying disease or condition (such as CHF), can all affect efficacy of an AF therapy. For example, pharmacological or electrostimulation rhythm control therapies can be less likely successful in patient experiencing permanent AF. In addition to the therapy type, therapy dosage or parameters that controls the strength or duration of therapy may also affect the AF therapy efficacy. Therefore, it is desirable to have an individualized AF therapy that effectively mitigates the adverse impact of AF episodes on a particular patient.

Efficacy of an AF therapy can be evaluated by examining whether the goal of treatment has been reached, being either a restoration of NSR or a regularization of ventricular contractions with reduced heart rate. However, atrial activity signal such as P wave in an electrocardiogram (ECG) can be a relatively weak signal compared to ventricular activity such as R wave or QRS complex which is produced by ventricular depolarization. Atrial activity signals can also be contaminated by noise, or interfered by various physiologic or environmental conditions. Although a dedicated atrial sensing such as by using an implanted lead placed in or near the atrium can improve atrial signal quality, it is not applicable to patient not indicated for atrial lead implantation. On the other hand, AF detection based on irregular ventricular contractions may suffer from confounding factors such as ventricular ectopic contracts or improper sensing of ventricular contractions, which may also manifest irregularity in R waves or QRS complexes. As such, evaluation of AF therapy efficacy based on atrial rate or regularity of ventricular contraction can be less reliable. Therefore, the present inventors have recognized that there remains a considerable need of systems and methods that can determine an individualized AF therapy and evaluate the efficacy of the individualized AF therapy.

Ambulatory medical devices (AMDs) can be used for monitoring HF patient and detecting HF worsening events. Examples of such ambulatory medical devices can include implantable medical devices (IMDs), subcutaneous medical devices, wearable medical devices or other external medical devices. The ambulatory or implantable medical devices can include physiologic sensors which can be configured to sense electrical activity and mechanical function of the heart, or physical or physiological variables associated with the signs and symptoms of worsening of HF. The medical device can optionally deliver therapy such as electrical stimulation pulses to a target area, such as to restore or improve the cardiac function or neural function.

Some AMDs can include a physiologic sensor that provides diagnostic features. In an example, an AMD can include an impedance sensor to sense the fluid status in the lungs. In another example, an AMD can include sensors for detecting heart sounds. Heart sounds are associated with mechanical vibrations from activity of a patient's heart and the flow of blood through the heart, thus are indicative of a patient's hemodynamic status. Heart sounds recur with each cardiac cycle and are separated and classified according to the activity associated with the vibration. The first heart sound (S1) is associated with the vibrational sound made by the heart during tensing of the mitral valve. The second heart sound (S2) marks the beginning of diastole. The third heart sound (S3) and fourth heart sound (S4) are related to filling pressures of the left ventricle during diastole.

The diagnostic feature provided by the physiologic sensors can indicate a patient's hemodynamic status. For example, heart sounds are useful indicators of proper or improper functioning of a patient's heart, and can be used to assess a patient's hemodynamic status. On the other hand, in patient developing an AF episode, the loss of normal AV synchrony and irregular ventricular rhythm can adversely impact the hemodynamic stability in the patient. The loss of effective atrial contraction may result in a marked decrease in cardiac output, especially for persons with impaired diastolic filling of the ventricles. An ongoing AF can cause more significant hemodynamic deterioration in patients with mitral stenosis, restrictive or hypertrophic cardiomyopathy, pericardial diseases, or ventricular hypertrophy. Therefore, physiologic sensors such as heart sounds sensors can be used to assess adverse hemodynamic impact of the AF event on a patient as well as the improvement of hemodynamic outcome in response to various AF therapies, and determine a desirable AF therapy based on the detected improvement in hemodynamic outcome. Various embodiments described herein can help determining an individualized therapy for treating AF or other atrial tachyarrhythmia episode in a patient or evaluating efficacy of the therapy.

Example 1 can include a system that comprises an AF detection circuit configured to detect an AF episode, one or more programmable therapy circuits configured to generate and deliver to the patient a respective therapy in response to the detection of the AF episode, and a hemodynamic sensor circuit configured to sense a hemodynamic status output indicative of a hemodynamic status of the patient. The system can include a therapy selection circuit coupled to the hemodynamic sensor circuit and the one or more programmable therapy circuit. In response to the detection of the AF episode, the therapy selection circuit can automatically program the one or more programmable therapy circuits to generate and sequentially deliver to the patient a first candidate therapy and a different second candidate therapy. The therapy selection circuit can receive from the hemodynamic sensor circuit a first value of the hemodynamic status output in response to or during the delivery of the first candidate therapy and a second value of the hemodynamic status output in response to or during the delivery of the second candidate therapy, and select a desired therapy based on the first and second values of the hemodynamic status output.

Example 2 can include, or can optionally be combined with the subject matter of Example 1 to optionally include: one or more programmable therapy circuits that can generate and deliver to the patient a respective therapy modality including one or more of a cardiac stimulation therapy, a cardiac ablation therapy, a neurostimulation therapy, a denervation therapy, or a pharmacological therapy; and a therapy selection circuit that can program the programmable therapy circuits to respectively generate and sequentially deliver to the patient the first and second candidate therapies each selected from the one or more of the cardiac stimulation therapy, the cardiac ablation therapy, the neurostimulation therapy, the denervation therapy, or the pharmacological therapy.

Example 3 can include, or can optionally be combined with the subject matter of Examples 2 to optionally include one or more programmable therapy circuits that can generate one or more of ventricular fallback pacing therapy, ventricular rate regularization pacing therapy, atrial anti-tachycardia pacing therapy, atrial cardioversion therapy, or atrial defibrillation therapy.

Example 4 can include, or can optionally be combined with the subject matter of one or any combination of Examples 1 through 3 to optionally include a second candidate therapy which can be of a different therapy modality than the first candidate therapy.

Example 5 can include, or can optionally be combined with the subject matter of one or any combination of Examples 1 through 3 to optionally include a second candidate therapy that differs from the first candidate therapy by at least one therapy parameter associated with therapy generation or configuration, such as a therapy dosage, a therapy duration, or a therapy strength.

Example 6 can include, or can optionally be combined with the subject matter of Examples 5 to optionally include in the first candidate therapy a ventricular fallback pacing therapy where the pacing rate gradually changes to a first lower rate limit (LRL) value within a first specified time period, and the second candidate therapy can be a ventricular fallback pacing therapy where the pacing rate gradually changes to a second LRL value different from the first LRL value within a second specified time period.

Example 7 can include, or can optionally be combined with the subject matter of one or any combination of Examples 1 through 6 to optionally include a therapy selection circuit that can program the one or more programmable therapy circuits to initiate the delivery of the second candidate therapy after a specified recovery time following a cessation of the delivery of the first candidate therapy.

Example 8 can include, or can optionally be combined with the subject matter of one or any combination of Examples 1 through 7 to optionally include in the hemodynamic sensor circuit a heart sound sensor configured to sense a heart sound (HS) signal and a hemodynamic parameter generator circuit configured to detect, using the HS signal, one or more HS components including an S1, an S2, or an S3 heart sound.

Example 9 can include, or can optionally be combined with the subject matter of Examples 8 to optionally include a hemodynamic parameter generator circuit that can determine a HS strength indicative of strength of the HS component including strength of the S1, the S2, or the S3 heart sound; and a therapy selection circuit that can receive, from the hemodynamic parameter generator circuit, a first value of the HS strength in response to or during the delivery of the first candidate therapy and a second value of the HS strength in response to or during the delivery of the second candidate therapy, and to select the first candidate therapy as the desired therapy if the first value of the HS strength is greater than the second value of the HS strength, or select the second candidate therapy as the desired therapy if the second value of the HS strength is greater than the first value of the HS strength.

Example 10 can include, or can optionally be combined with the subject matter of Examples 8 to optionally include a cardiac activity sensor configured to sense a cardiac electrical activity including atrial depolarization or ventricular depolarization. The hemodynamic parameter generator circuit can be used to determine a diastolic timing interval (DTI) using the sensed cardiac electrical activity and the detected HS component; and the therapy selection circuit can receive, from the hemodynamic parameter generator circuit, a first value of DTI in response to or during the delivery of the first candidate therapy and a second value of DTI in response to or during the delivery of the second candidate therapy, and to select the first candidate therapy as the desired therapy if the first value of DTI is greater than the second value of DTI, or select the second candidate therapy as the desired therapy if the second value of DTI is greater than the first value of DTI.

Example 11 can include, or can optionally be combined with the subject matter of Examples 8 to optionally include a cardiac activity sensor configured to sense a cardiac electrical activity including atrial depolarization or ventricular depolarization, wherein the hemodynamic parameter generator circuit can calculate a variability of cardiac timing interval (CTIvar) using the sensed cardiac electrical activity and the detected HS component.

Example 12 can include, or can optionally be combined with the subject matter of Examples 11 to optionally include a hemodynamic parameter generator circuit that can determine the CTIvar including a variability of diastolic timing interval (DTIvar); and a therapy selection circuit that can receive a first value of DTIvar in response to or during the delivery of the first candidate therapy and a second value of DTIvar in response to or during the delivery of the second candidate therapy, and to select the first candidate therapy as the desired therapy if the first value of DTIvar is lower than the second value of DTIvar, or select the second candidate therapy as the desired therapy if the second value of DTIvar is lower than the first value of DTIvar.

Example 13 can include, or can optionally be combined with the subject matter of one or any combination of Examples 1 through 12 to optionally include a therapy selection circuit that can, prior to the delivery of the first and second candidate therapies, receive from the hemodynamic sensor circuit a pre-therapy hemodynamic status output and determine a level of hemodynamic deterioration including a relative change of hemodynamic status in response to the detected AF event, and program the one or more programmable therapy circuits to generate respectively the first and second candidate therapies based on the level of hemodynamic deterioration.

Example 14 can include, or can optionally be combined with the subject matter of one or any combination of Examples 1 through 12 to optionally include a therapy selection circuit that can receive from the hemodynamic sensor circuit a first value of pre-therapy hemodynamic status output before the delivery of the first candidate therapy, and a second value of pre-therapy hemodynamic status output before the delivery of the second candidate therapy; and select a desired therapy based on the first and second values of the hemodynamic status output and the first and second pre-therapy hemodynamic status outputs.

Example 15 can include, or can optionally be combined with the subject matter of Examples 14 to optionally include a therapy selection circuit that can calculate a first relative change from the first pre-therapy hemodynamic status output to the first value of the hemodynamic status output, and a second relative change from the second pre-therapy hemodynamic status output to the second value of the hemodynamic status output; and to select the first candidate therapy as a desired therapy if the first relative change is greater than the second relative change, or select the second candidate therapy as the desired therapy if the second relative change is greater than the first relative change.

Example 16 can include processes of detecting an AF onset event in the patient. When the AF onset event is detected, a first candidate therapy can be automatically programmed and delivered to the patient, and a first value of a hemodynamic status parameter can be sensed from the patient in response to or during the delivery of the first candidate therapy. A second candidate therapy can then be automatically programmed and delivered to the patient, and a second value of a hemodynamic status parameter can be sensed from the patient in response to or during the delivery of the second candidate therapy. The method includes a process of determining a desired therapy based on the first and second values of the hemodynamic status output. In an embodiment, a candidate therapy that leads to more significant improvement in the patient's hemodynamic status can be selected as the desired AF therapy.

Example 17 can include, or can optionally be combined with the subject matter of Examples 16 to optionally include generating first and second candidate therapies each selected from one or more of a cardiac stimulation therapy, a cardiac ablation therapy, a neurostimulation therapy, a denervation therapy, or a pharmacological therapy, wherein the cardiac stimulation therapies can include one or more of ventricular fallback pacing therapy, ventricular rate regularization pacing therapy, atrial anti-tachycardia pacing therapy, atrial cardioversion therapy, or atrial defibrillation therapy.

Example 18 can include, or can optionally be combined with the subject matter of one or any combination of Examples 1 and 17 to optionally include generating a second candidate therapy different from the first candidate therapy by at least one therapy parameter associated with therapy generation or configuration, the at least one therapy parameter including a therapy dosage, a therapy duration, or a therapy strength.

Example 19 can include, or can optionally be combined with the subject matter of one or any combination of Examples 16 through 18 to optionally include sensing a heart sound (HS) strength indicative of strength of an S1, an S2, or an S3 heart sound, and selecting the first candidate therapy as the desired therapy if the first value of the HS strength is greater than the second value of the HS strength, or selecting the second candidate therapy as the desired therapy if the second value of the HS strength is greater than the first value of the HS strength.

Example 20 can include, or can optionally be combined with the subject matter of one or any combination of Examples 16 through 18 to optionally include sensing a cardiac electrical activity including atrial depolarization or ventricular depolarization and sensing HS component including an S1, an S2, or an S3 heart sound, the hemodynamic status parameter including a diastolic timing interval (DTI) determined using the sensed, cardiac electrical activity and the sensed HS component, and selecting the first candidate therapy as the desired therapy if the first value of the DTI is greater than the second value of the DTI, or selecting the second candidate therapy as the desired therapy if the second value of the DTI is greater than the first value of the DTI.

Example 21 can include, or can optionally be combined with the subject matter of one or any combination of Examples 16 through 18 to optionally include sensing a cardiac electrical activity including sensing an atrial depolarization or ventricular depolarization and sensing a HS component including an S1, and S2, or an S3 heart sound, and sensing a hemodynamic status parameter including a variability of cardiac timing interval (CTIvar) determined using the sensed cardiac electrical activity and the sensed HS component.

Example 22 can include, or can optionally be combined with the subject matter of Example 21 to optionally include sensing a first value of variability of diastolic timing interval (DTIvar) in response to or during the delivery of the first candidate therapy, sensing a second value of DTIvar in response to or during the delivery of the second candidate therapy, and electing the first candidate therapy as the desired therapy if the first value of DTIvar is lower than the second value of DTIvar, or select the second candidate therapy as the desired therapy if the second value of DTIvar is lower than the first value of DTIvar.

Example 23 can include, or can optionally be combined with the subject matter of one or any combination of Examples 16 through 18 to optionally include sensing a pre-therapy hemodynamic status output and determining a level of hemodynamic deterioration before the delivery of the first and second candidate therapies, wherein automatically programming the first and second candidate therapies includes programming the first and second candidate therapies based on the level of hemodynamic deterioration.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for treating atrial tachyarrhythmias such as atrial fibrillation (AF). By monitoring a patient's hemodynamic sensor response to one of a plurality of candidate AF therapies such as using a heart sound sensor, the systems and methods discussed in the present document can be used in selecting a patient-specific AF therapy that provides a desirable hemodynamic effect. The systems and methods discussed in this document can also be used for evaluating efficacies of various therapies for treating other types of atrial tachyarrhythmias such as atrial tachycardia or atrial flutter.

Figure 1:
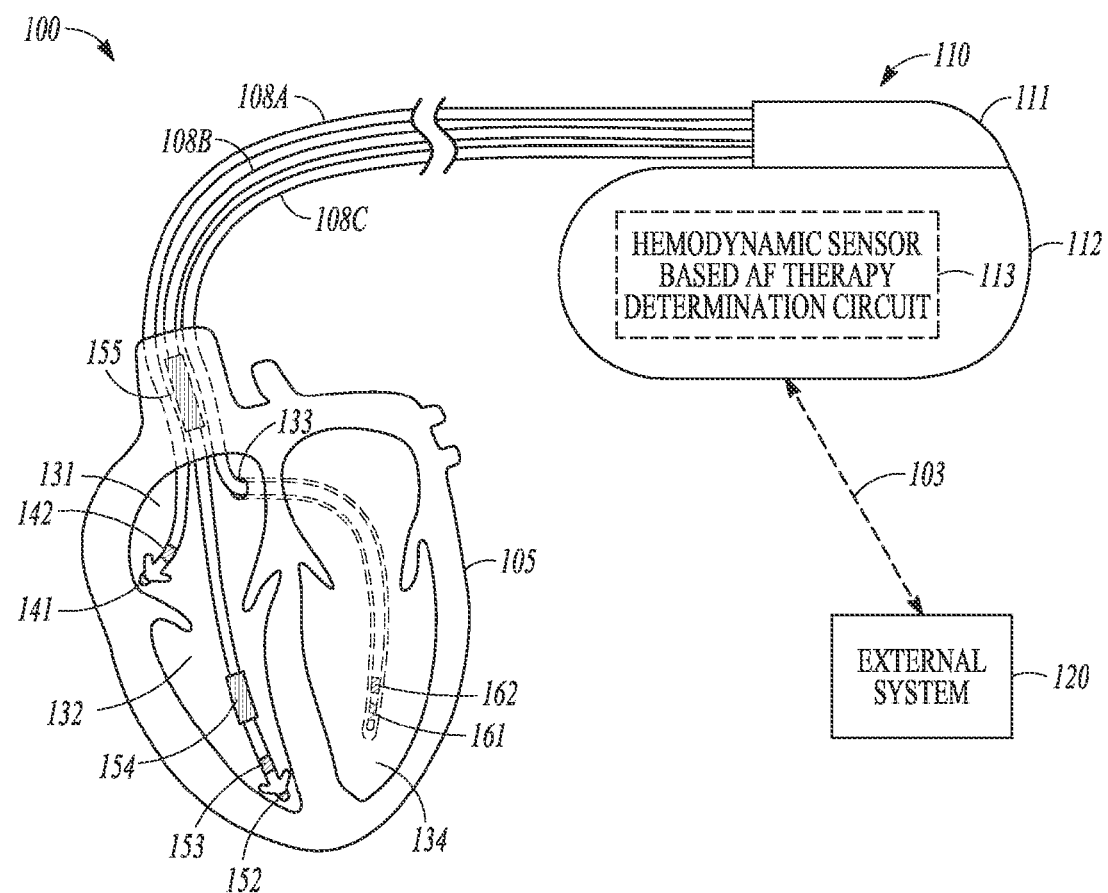
FIG. 1 illustrates an example of a cardiac rhythm management (CRM) system and portions of the environment in which the CRM system operates.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, a diagnostic device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 1155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the MID 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the MID 110 such as via separate conductors in the lead 108C such as to allow for sensing of the LV electrogram and optionally allow delivery of one or more resynchronization pacing pulses from the LV.

The IMD 110 can include an electronic circuit that can sense a physiological signal. The physiological signal can include an electrogram or a signal representing mechanical function of the heart 105. The hermetically seated can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are possible.

As illustrated, the CRM system 100 can include a hemodynamic sensor-based AF therapy determination circuit 113.

The hemodynamic sensor-based AF therapy determination circuit 113 can be configured to determine a desirable therapy from a plurality of candidate AF therapies based on impact of the therapy on the patient's hemodynamic status. The candidate AF therapies can include therapies of different modalities or types, or therapies of the same type or modality but different parameter settings associated with therapy dosage, strength, or therapy duration. Examples of the hemodynamic sensor-based AF therapy determination circuit 113 are described below, such as with reference to FIGS. 2-3.

The external system 120 can allow for programming of the IMD 110 and can receive information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an interact connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to IMD 110 such as to configure the IMD 110 to perform one or more actions that can include physiological data acquisition such as using programmably specifiable sensing electrodes and configuration, device self-diagnostic test, or delivery of one or more therapies.

The hemodynamic sensor-based AF therapy determination circuit 113 can be implemented at the external system 120 such as using data extracted from the IMD 110 or data stored in a memory within the external system 120. Portions of the hemodynamic sensor-based AF therapy determination circuit 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
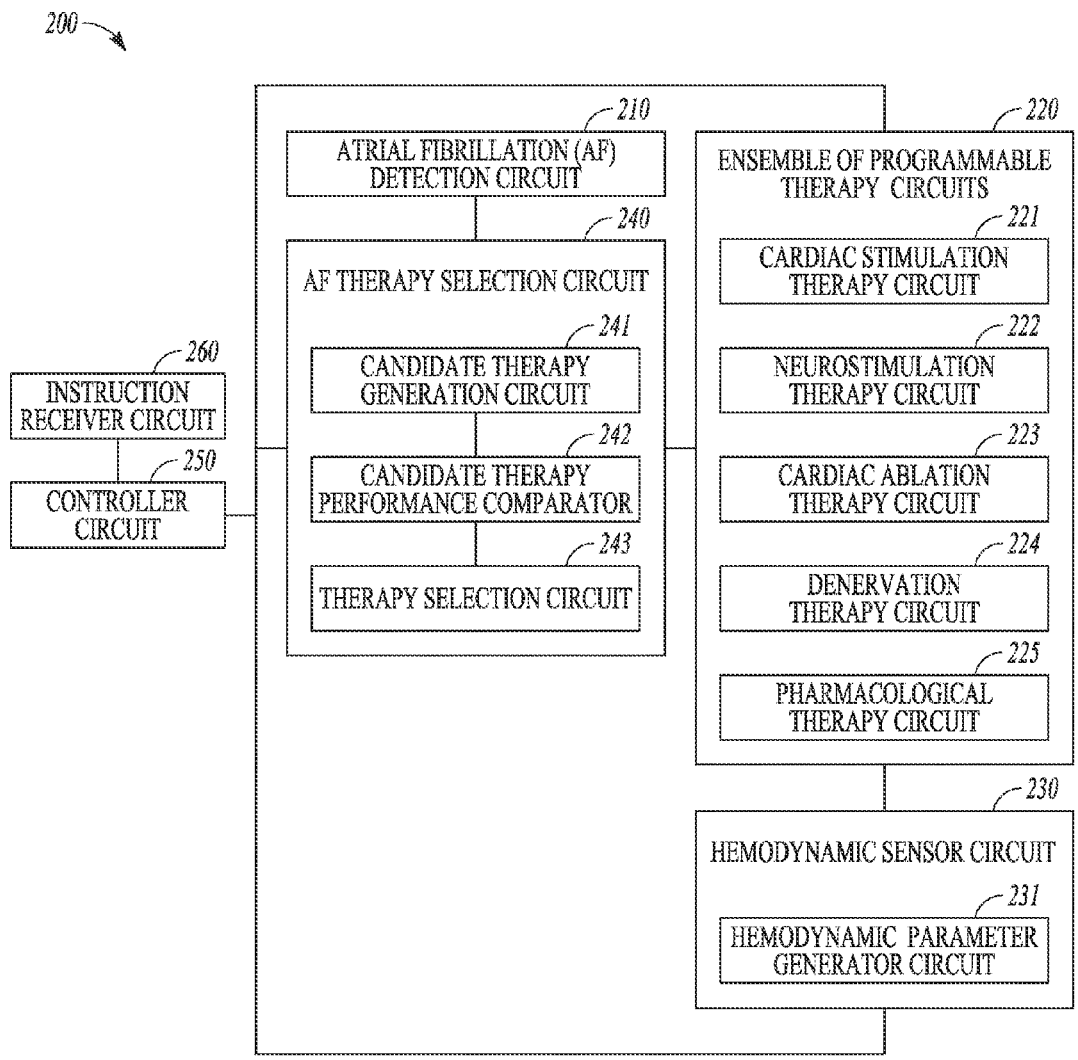
FIG. 2 illustrates an example of a hemodynamic sensor-based AF therapy determination circuit.

FIG. 2 illustrates an example of a hemodynamic sensor-based AF therapy determination circuit 200, which can be an embodiment of the hemodynamic sensor-based AF therapy determination circuit 113. The hemodynamic sensor-based physiologic event detector circuit 200 can include one or more of an atrial fibrillation (AF) detection circuit 210, an ensemble of programmable therapy circuits 220, a hemodynamic sensor circuit 230, an AF therapy selection circuit 240, a controller circuit 250, and an instruction receiver circuit 260.

The AF detection circuit 210 can be configured to detect an AF event from a patient. The AF detection circuit 210 can be coupled to one or more physiologic sensors each configured to sense a physiologic signal indicative of presence of an AF episode. Examples of such physiologic signals can include electrocardiograms (ECGs) such as sensed by using electrodes non-invasively attached to the body surface, subcutaneous ECGs such as sensed by using subcutaneously placed electrodes, or intracardiac electrograms (EGMs) such as sensed by using electrodes on one or more of the leads 108A-C or the can 112. The physiologic signals can also include signals indicative of cardiac mechanical activities such as contractions of an atrium or a ventricle. The cardiac mechanical activities can include a signal sensed from an ambulatory accelerometer or a microphone configured to sense the heart sounds in a patient. The cardiac mechanical activities can include a signal sensed from an impedance sensor configured to sense intracardiac impedance change as a result of cyclic cardiac contractions. The AF detection circuit 210 can detect from the sensed physiologic signals atrial electrical events (such as P waves) or mechanical events, and ventricular electrical events (such as R waves or QRS complexes) or mechanical events, and detect an AF onset event when the atrial electrical or mechanical events or the ventricular electrical or mechanical events respectively meets a specified criterion. In an example, the AF detection circuit 210 can detect an AF onset event when the atrial rate exceeds a specified atrial rate threshold, in another example, the AI detection circuit 210 can detect an AF onset event when the ventricular rate exceeds a specified ventricular rate threshold and the variability of the ventricular rate exceeds a specified variability threshold.

The ensemble of programmable therapy circuits 220 can include one or more programmable therapy circuits each configured to generate and deliver to the patient a specified therapy in response to the detection of the AF event. Various therapy modalities with different procedures involved, type of energy used, or active agents in the therapy can be delivered. As illustrated in FIG. 2, the ensemble of programmable therapy circuits 220 can include one or more of a cardiac pacing therapy circuit 221, a neurostimulation therapy circuit 222, a cardiac ablation therapy circuit 223, a denervation therapy circuit 224, or a pharmacological therapy circuit 225. Additional therapy circuits configured to generate other therapy modalities can also be included in the ensemble of programmable therapy circuits 220.

The one or more programmable therapy circuits, either through wired or wireless link, can be communicatively coupled to a specified therapy delivery unit that interfaces with patient at respective therapy delivery sites. The therapy delivery unit can be within or external to the IMD 110. Each of the programmable therapy circuits can include a control unit that controls the therapy strength, dosage, duration, or other parameters associated with therapy generation, as well as configuration of the therapy deliver such as selection of electrodes for delivering the therapy energy to a target tissue. For example, the cardiac stimulation therapy circuit 221, through its control unit, can generate cardiac electrostimulation pulses with specified pulse amplitude, pulse waveform, pulse frequency, pulse width, duty cycle, duration, or any other parameters associated with the electrostimulation. The control unit of the cardiac stimulation therapy circuit 221 can also programmably control the delivery of the cardiac stimulation therapy in a specified electrode configuration including an anode and a cathode for interacting with the target cardiac tissue. One example of the cardiac stimulation therapy is ventricular fallback pacing, where the ventricular pacing rate, in response to the detection of AF event, gradually changes to a specified lower rate limit (LRL), and maintains at the rate of LRL until an AF termination event is detected or when a ventricular fallback pacing is terminated. Other examples of cardiac stimulation therapy can include one or more of ventricular rate regularization pacing therapy, atrial anti-tachycardia pacing therapy, atrial cardioversion therapy, or atrial defibrillation therapy, among others.

Likewise, the neurostimulation therapy circuit 222, through its control unit, can generate a neurostimulation sequence with specified therapy parameters including one or more of pulse amplitude, pulse waveform, pulse frequency, pulse width, duty cycle, duration, or any other parameters associated with the electrostimulation. The neurostimulation therapy circuit 222 can also configure electrodes used for delivering the neurostimulation pulses to the target neural tissue. The target neural tissue can include fat pads, atrioventricular node, or vagus nerve, among other neural targets.

The cardiac ablation therapy circuit 223 can programmably control the delivery of cardiac ablation energy to a target tissue such as an atrial tissue or AV node. The denervation therapy circuit 224 can programmably modulate connection of a nerve (such as a renal nerve or a vagus nerve) by at least partially blocking the nerve conduction surgically, pharmacologically, or electrically. The pharmacological therapy circuit 225 can programmably control the delivery of the pharmacological agents, such as through an automated ambulatory drug delivery system, to a target site in the patient.

The hemodynamic sensor circuit 230 can be configured to sense a hemodynamic status output indicative of a hemodynamic status of the patient. The hemodynamic sensor circuit 230 can be coupled, through wired or wireless link, to a hemodynamic sensor deployed on or inside the patient's body. The hemodynamic sensor can include implantable, wearable, or otherwise ambulatory physiologic sensors that directly or indirectly measures dynamics of the blood flow in the heart chambers or in the blood vessels. Examples of the hemodynamic sensor and the physiologic variables to sense can include pressure sensors configured for sensing arterial pressure, pulmonary artery pressure, left atrial pressure, RV pressure, LV coronary pressure; impedance sensors configured for sensing thoracic impedance or cardiac impedance; temperature sensor configured for sensing blood temperature; accelerometers or microphones configured for sensing one or more heart sounds; optical sensors such as pulse oximeters configured for sensing blood oxygen saturation; chemical sensors configured for sensing central venous pH value. In an example, the sensing of hemodynamic status output and generation of hemodynamic parameters are initiated in response to an automatically generated hemodynamic sensing command signal. The hemodynamic sensing command can be issued in response to the detection of an AF onset event such as provided by the AF detection circuit 210.

The hemodynamic sensor circuit 230 can include a hemodynamic parameter generator circuit 231 configured to generate one or more hemodynamic parameters from a plurality of measurements of a physiologic variable such as measured from different time instants. The hemodynamic parameters can include a statistical index derived from the plurality of measurements of the physiologic variables, such as mean, median or other central tendency measures, or second order statistics including variance or standard deviation of the measurements, a histogram of the hemodynamic parameter intensity, or higher order statistics of the measurements. Alternatively, or additionally, the hemodynamic parameter generator circuit 231 can generate a hemodynamic parameter using one or more signal trends of the physiologic parameter such as intensity of the physiologic parameter over time), one or more signal morphological descriptors, or signal power spectral density at a specified frequency range. Examples of hemodynamic sensor circuit 230 are described below, such as with reference to FIG. 3.

The hemodynamic sensor circuit 230 can be coupled to one or more programmable therapy circuits in the ensemble of programmable therapy circuits 220. In response to or during delivery of a therapy such as through one of the programmable therapy circuits, the hemodynamic sensor circuit 230 can sense a hemodynamic status output from the patient, and generate one or more hemodynamic parameters such as by using the hemodynamic parameter generator circuit 231. In some examples, a plurality of therapies can be delivered sequentially to the patient using one or more of the programmable therapy circuits, and the hemodynamic sensor circuit 230 can sense the respective hemodynamic status output and generate respective hemodynamic parameters in response to or during the delivery of each of the plurality of therapies.

The AF therapy selection circuit 240 can be coupled to the AF detection circuit 210, the ensemble of programmable therapy circuits 220, and the hemodynamic sensor circuit 230. The AF therapy selection circuit 240 can include a candidate therapy generation circuit 241, a candidate therapy performance comparator 242, and a therapy selection circuit 243.

The candidate therapy generation circuit 241 can automatically program one or more therapy circuits in the ensemble of programmable therapy circuits 220, generate two or more candidate therapies using the one or more programmable therapy circuits, and command the respective programmable therapy circuits to deliver the candidate therapies sequentially to the patient. In an example, the candidate therapy generation circuits 241 receives an indication of detection of AF onset from the AF detection circuit 210, and generate at least first and second candidate therapies using the one or more programmable therapy circuits in response to a detection of the AF onset. The candidate therapy generation circuit 241 can automatically program one or more therapy circuits based on a level of hemodynamic deterioration in response to the detected AF event. In an example, the candidate therapy generation circuit 241 can receive from the hemodynamic sensor circuit 230 a pre-therapy hemodynamic status output and establish a baseline hemodynamic status as the pre-therapy hemodynamic status output. The candidate therapy generation circuit 241 can determine a relative change of the hemodynamic status from the baseline hemodynamic status to the hemodynamic status during the detected AF event. Such a relative change can indicate an impact of the AF event on the hemodynamic deterioration. The candidate therapy generation circuit 241 can program the one or more programmable therapy circuits to generate respective candidate therapies with one or more of higher dosage, longer duration, or stronger therapy strength (such as more energy delivered) if a more severe hemodynamic deterioration is detected during the AF event.

The candidate therapy generation circuit 241 can control the sequential delivery of the candidate therapies in a specified order. In an example, the therapy order can be determined based on empirical knowledge about relative efficacy of mitigating adverse hemodynamic outcome among the candidate therapies. The empirical knowledge can include population-based therapy efficacy data or a record of therapy performance from a patient's therapy history. A candidate therapy that is more likely (based on empirical data) to result in a better hemodynamic improvement can be delivered before another therapy that is less likely to improve the hemodynamic status in the patient.

The candidate therapies can be generated using different programmable therapy circuits, such that the candidate therapies differ from each other in therapy modalities or types. For example, the candidate therapy generation circuit 241 can automatically program the first candidate therapy to be a cardiac pacing therapy with specified programming parameters using the cardiac stimulation therapy circuit 221, and program the second candidate therapy to be a vagus nerve stimulation therapy with specified programming parameters using the neurostimulation therapy circuit 222. In another example, at least two of the candidate therapies can be generated using the same programmable therapy circuit, such that the first and second candidate therapies can have the same therapy modality, but different strength, dosage, duration, stimulation site, or other stimulation configurations. For example, the candidate therapy generation circuit 241 can automatically program the first candidate therapy to be a ventricular rate regularization pacing therapy, and program the second candidate therapy to be an atrial antitachycardia pacing therapy. In another example, the candidate therapy generation circuit 241 can automatically program both the first and second candidate therapies to be ventricular fallback pacing differing by at least one therapy parameter. For example, the first candidate therapy is a ventricular fallback pacing therapy where the pacing rate gradually changes to a first LRL value, while the second candidate therapy is a ventricular fallback pacing therapy where the pacing rate gradually changes to a second LRL value different than the first LRL value.

The candidate therapy generation circuit 241 can control the one or more programmable therapy circuits to terminate respective candidate therapies when specified conditions are met. In an example, the candidate therapy generation circuit 241 can receive from the hemodynamic sensor circuit 230 information about changes in hemodynamic status during the delivery of a candidate therapy. Before the scheduled timeout of the candidate therapy (which can be programmed into the corresponding candidate therapy circuit), the candidate therapy generation circuit 241 can issue a command to the corresponding candidate therapy circuit to terminate the ongoing candidate therapy if the improvement of hemodynamic status has exceeded a threshold level. The candidate therapy generation circuit 241 can also issue a command to terminate the ongoing candidate therapy if the degree of hemodynamic recovery or the rate of hemodynamic recovery fails to reach a respective threshold level, which is suggestive of ineffectiveness of the candidate therapy.

The candidate therapy performance comparator circuit 242, coupled to the hemodynamic sensor circuit 230, can receive hemodynamic information including the hemodynamic parameters such as provided by the hemodynamic parameter generator circuit 231 generated during or in response to delivery of one or more candidate therapies. The hemodynamic parameters measured during the delivery of a candidate therapy can indicate effect of the candidate therapy in mitigating the adverse hemodynamic impact caused by the AF episode, thereby suggestive of efficacy of the candidate therapy. The candidate therapy performance comparator circuit 242 can compare the hemodynamic parameters corresponding to different candidate therapies. The therapy selection circuit 243, by using the hemodynamic parameters measured during different candidate therapies, can choose a desirable therapy among the candidate therapies according to a specified criterion. In an example, the therapy selection circuit 243 can determine a desirable therapy as the candidate therapy that yields the highest value of the hemodynamic parameters indicating most significant hemodynamic recovery among the candidate therapies. In another example, the therapy selection circuit 243 can determine a desirable therapy as the candidate therapy that results in fastest hemodynamic recovery in response to or during the delivery of the candidate therapy indicating most significant responsiveness among the candidate therapies.

In some examples, the candidate therapy performance comparator circuit 242 can separate the candidate therapies into different categories and separately compare the hemodynamic parameters corresponding to candidate therapies within the same therapy category (i.e., the "intra-category" hemodynamic parameter comparison); and the therapy selection circuit 243 can choose a desirable therapy using both the distinction among the therapy categories and the intra-category hemodynamic parameter comparison of each therapy category. For example, the candidate therapies can include a reversible therapy group and an irreversible therapy group. The reversible therapy group can include, for example, cardiac pacing therapies such as provided by the cardiac stimulation therapy circuit 221 and neurostimulation therapy such as provided by the neurostimulation therapy circuit 222. The irreversible therapy group can include, for example, cardiac ablation therapies such as provided by the cardiac ablation therapy circuit 223, denervation therapy such as provided by the denervation therapy circuit 224, and pharmacological therapy such as provided by the pharmacological therapy circuit 225. The candidate therapy performance comparator circuit 242 can compare the hemodynamic parameters corresponding to the candidate therapies in the reversible therapy group, and separately compare the hemodynamic parameters corresponding to the candidate therapies in the irreversible therapy group. The therapy selection circuit 243 can prioritize the reversible therapy category over the irreversible therapy category, and choose from the reversible therapy group a desirable therapy that yields the highest value of the hemodynamic parameter indicating most significant hemodynamic recovery during AF. However, if all available reversible therapies fail to sufficiently mitigate the hemodynamic deterioration due to AF (such as failing to meet a hemodynamic recovery criterion), the therapy selection circuit 243 can choose from the irreversible therapy group a therapy that yields the highest value of the hemodynamic parameter indicative of most significant hemodynamic recovery during AF. In some examples, the candidate therapy generation circuit 241 can sequentially deliver the candidate therapies in the reversible therapy group in an order based on empirical knowledge such as historical performance of the candidate therapies in a patient population. The therapy selection circuit 243 can determine if the hemodynamic recovery upon delivery of a first reversible therapy in the ordered therapy sequence meets a hemodynamic recovery criterion. If the first reversible therapy meets the hemodynamic recovery criterion, the therapy selection circuit 243 can choose the first reversible therapy as the desirable therapy. Otherwise, a second reversible therapy from the ordered therapy sequence can be delivered, and the therapy selection circuit 243 can assess if the second reversible therapy meets the hemodynamic recovery criterion.

In an example where the hemodynamic sensor circuit 230 includes a heart sound (HS) sensor for detecting one or more HS components such as S1, S2, S3 or S4 heart sounds, the hemodynamic parameter generator circuit 231 can generate a feature of HS intensity, and the therapy selection circuit 243 can receive, from the hemodynamic parameter generator circuit 231, a first value of the HS intensity ($\|HS\|_{i1}$) in response to or during the delivery of the first candidate therapy and a second value of the HS intensity ($\|HS\|_{i2}$) in response to or during the delivery of the second candidate therapy. The candidate therapy performance comparator 242 compares $\|HS\|_{i1}$ to $\|HS\|_{i2}$, and the therapy selection circuit 243 can choose the first candidate therapy to be the desirable therapy if the $\|HS\|_{i1}$ is greater than the $\|HS\|_{i2}$, or select the second candidate therapy to be the desirable therapy if $\|HS\|_{i2}$ is greater than the $\|HS\|_{i1}$. In another example, the hemodynamic parameter generator circuit 231 can generated a feature of cardiac timing interval (CTI) such as a diastolic timing interval (DTI), and the therapy selection circuit 243 can receive, from the hemodynamic parameter generator circuit 231, a first value of DTI ($DT_{I1}$) in response to or during the delivery of the first candidate therapy and a second value of DTI ($DT_{I2}$) in response to or during the delivery of the second candidate therapy. The candidate therapy performance comparator 242 compares $DT_{I1}$ to $DT_{I2}$, and the therapy selection circuit 243 can choose the first candidate therapy to be the desirable therapy if the $DT_{I1}$ is greater than the $DT_{I2}$, or select the second candidate therapy to be the desirable therapy if the $DT_{I2}$ is greater than the $DT_{I1}$. In another example, the hemodynamic parameter generator circuit 231 can generated a feature of variability of cardiac timing interval (CTIvar), such as a variability of systolic timing interval (STIvar) or a variability of diastolic timing interval (DTIvar). The candidate therapy performance comparator 242 can compare a first value of DTIvar ($DTIva_{r1}$) in response to or during the delivery of the first candidate therapy to a second value of DTIvar ($DTIva_{r2}$) in response to or during the delivery of the second candidate therapy. The therapy selection circuit 243 can select the first candidate therapy to be the desirable therapy if the $DTIva_{r1}$ is smaller than the $DTIva_{r2}$, or select the second candidate therapy to be the desirable therapy if the $DTIva_{r2}$ is smaller than the $DTIva_{r1}$. Examples of heart sound sensor and the hemodynamic parameter extraction including $\|HS\|$, CTI, or CTIvar using the heart sound signal are described below, such as with reference to FIG. 3.

The controller circuit 250 can receive external programming input from the instruction receiver circuit 260 to control the operations of the AF detection circuit 210, the ensemble of programmable therapy circuits 220, the hemodynamic sensor circuit 230, the AF therapy selection circuit 240, and the data flow and instructions between these components. Examples of the instructions received by instruction receiver 260 can parameter used in detecting an AF onset event, sensing one or more of hemodynamic status signals, extracting hemodynamic parameters, confirming or modifying the automatically candidate therapies, or confirming or modifying the automatically determined desirable therapy. The instruction receiver circuit 260 can include a user interface configured to present programming options to the user and receive system user's programming input. In an example, at least a portion of the instruction receiver circuit 260, such as the user interface, can be implemented in the external system 120.

Figure 3:
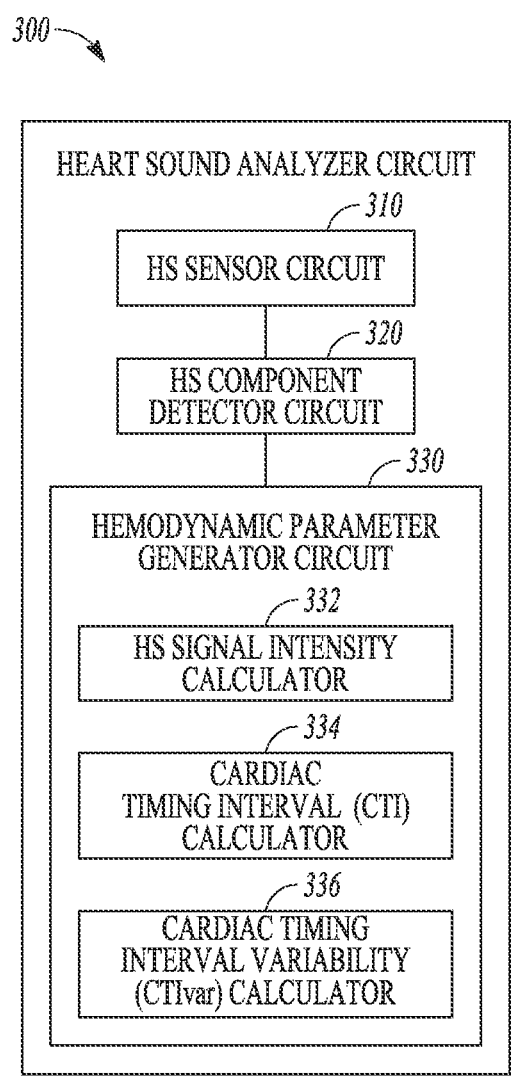
FIG. 3 illustrates an example of a heart sound analyzer circuit.

FIG. 3 illustrates an example of a heart sound (HS) analyzer circuit 300, which can be an embodiment of the hemodynamic sensor circuit 230. The HS analyzer circuit 300 can be configured to sense a HS signal and generate one or more HS features indicative or correlative of hemodynamic status of the patient. In various examples, the HS analyzer circuit 300 can sense the HS signal at specified time or in response to a command or a triggering event, such as before AF detection, during a detected AF event but prior to any therapy delivery, or during a delivery of a specified therapy. The HS analyzer circuit 300 can include a HS sensor circuit 310, a HS component detector circuit 320, and a hemodynamic parameter generator circuit 330.

The HS sensor circuit 310 can be coupled to a heart sound sensor that can detect the heart sound or other forms of signals generated as a result of mechanical activities of the heart such as contraction and relaxation. Examples of the HS sensors can include an ambulatory accelerometer or an ambulatory microphone. The heart sound sensor can be external to the patient or implanted inside the body. In an example, the heart sound sensor can be within an ambulatory medical device such as the IMD 110.

The HS component detector circuit 320 can be configured to process the sensed HS signal, including amplification, digitization, filtering, or other signal conditioning operations. In an example, the HS component detector circuit 320 can include one or more signal filters that can filter the sensed HS signal to a specified frequency range. For example, the HS component detector circuit 320 can include a bandpass filter adapted to filter the HS signal to a frequency range of approximately between 5 and 90 Hz. In another example, the HS component detector circuit 320 includes a bandpass filter adapted to filter the HS signal to a frequency range of approximately between 9 and 90 Hz. In an example, the HS component detector circuit 320 can include a double or higher-order differentiator configured to calculate a double or higher-order differentiation of the sensed heart sound signal.

The HS component detector circuit 320 can further detect, using the processed HS signal, one or more HS components including S1, S2, S3 or S4 heart sounds. In an example, the HS component detector circuit 320 can generate respective time windows for detecting one or more HS components. The time windows can be determined with reference to a physiologic event such as Q wave, R wave, or QRS complexes detected from a surface ECG, a subcutaneous ECG, or cardiac sensing events in an intracardiac EGM. For example, an S1 detection window can begin at 50 milliseconds (msec) following a detected R wave and have a duration of 300 msec. An S2 detection window can begin at specified offset following a detected R wave or S1 heart sound. An S3 detection window can be determined using at least one cardiac signal feature such as the R-wave timing or the timing of S2 heart sound. The S3 detection window can have a specified duration and can begin at a specified offset following the detected S2. In an example, the offset can be 125 msec, and the S3 window duration can be 125 msec. The offset or the S3 window duration can be a function of a physiologic variable such as a heart rate. For example, the offset can be inversely proportional to the heart rate, such that the S3 detection window can start at a smaller offset following the S2 at a higher heart rate.

The HS component detector circuit 320 can detect an HS component from at least a portion of the HS signal within the respective HS detection window. In an example, HS signal energy within a S2 detection window can be computed and compared to a S2 energy threshold, and an S2 component is detected in response to the HS signal energy exceeds the S2 energy threshold. In an example, the HS component detector circuit 320 can detect an HS component adaptively by tracking the temporal locations of the previously detected HS features. For example, an S3 heart sound can be detected by adaptively tracking the timing of historically detected S3 heart sounds. A dynamic programming algorithm can be used to detect and track the S3 heart sound within the S3 detection window, such as that disclosed in the commonly assigned Patangay et al. U.S. Pat. No. 7,853,327 entitled "HEART SOUND TRACKING SYSTEM AND METHOD," which is hereby incorporated by reference in its entirety.

The hemodynamic parameter generator circuit 330 can generate one or more hemodynamic parameters using the HS components such as one or more of S1, S2, S3, or S4 heart sounds. As illustrated in FIG. 3, The hemodynamic parameter generator circuit 330 can include a HS signal intensity calculator 332 configured to calculate an HS intensity indicative of strength of a HS component, such as intensity of an S1 heart sound ($\|S1\|$) or intensity of S2 heart sound ($\|S2\|$). Examples of the intensity of a HS component can include amplitude of a detected HS component in a time-domain HS signal, a transformed HS signal such as integrated HS energy signal, or in a frequency-domain HS signal such as the peak value of the power spectral density. In some examples, the hemodynamic parameter generator circuit 330 can be configured to measure the HS intensity as the peak value of a generic measurement within the respective HS detection window, such as peak envelop signal or root-mean-squared value of the portion of the HS signal within the HS detection window. During AF, HS intensity can be reduced, resulting in deterioration of hemodynamic status. A therapy that leads to recovery of HS intensity such as $\|S1\|$ or $\|S2\|$ therefore can indicate more effective mitigation of the adverse hemodynamic outcome in AF. Examples of HS intensity during the AF onset and in response to an AF therapy are described below, such as with reference to FIG. 4.

The hemodynamic parameter generator circuit 330 can alternatively or additionally include a cardiac timing interval calculator 334 configured to determine a cardiac timing interval (CTI) using the sensed cardiac electrical activity and the detected HS component. The CTI represents the timing interval between two cardiac events such as a cardiac electrical event detected from the cardiac electrical signal and a mechanical event such as detected from a cardiac mechanical signal or a hemodynamic signal such as heart sound signal.

The CTI can include a pre-ejection period (PEP), a systolic timing interval (STI), a left-ventricular ejection time (LVET), or a diastolic timing interval (DTI), among others. The PEP represents the total duration of the electrical and mechanical events prior to ejection. The PEP can include the electrical-mechanical delay which occurs between the onset of the ventricular depolarization and the beginning of ventricular contraction, and the isovolumetric contraction time during which the left ventricle can contract prior to the opening of the aortic valve. The PEP can be measured using one or more physiologic signals. In an example, the PEP can be measured as the time duration from the onset of the QRS to the S1 heart sound, that is, PEP≈Q–S1 interval. The onset of the QRS can be determined from the ECG as the Q wave or the atrial activation event from the EGM such as the atrial EGM measured using one or more electrodes on the implantable lead 108A and the can 112. In another example, the PEP can be measured as the duration from the Q wave or the atrial activation event to the rise of the arterial pressure such as that measured from a carotid pulse wave. In an example, when no spontaneous QRS wave is present and the heart is electrically paced such as by using an IMD 110, the PEP can be measured from the ventricular pacing (Vp) signal to the beginning of ventricular ejection such as represented by the onset of S1 heart sound, that is, PEP≈Vp−S1 interval.

The STI represents the duration of total electro-mechanical systole. The STI spans from the electrical excitation of the heart to the closure of the aortic valve, and it contains two major components, namely the PEP and the LVET, which represents the time interval from the opening to the closing of the aortic valve (mechanical systole). In an example, LVET can be measured as the period from S1 to S2 heart sounds. The STI can be measured using one or more physiologic signals sensed from physiologic sensors. Examples of the physiologic signals used for calculating STI or LVET include a heart sound signal, an intracardiac impedance signal, or a pressure signal. In an example, the STI can be measured as the interval from the onset of the QRS complex on the ECG or the atrial activation event in an intracardiac EGM to the S2 heart sound, that is, STI≈Q−S2 interval. In the case when the ventricle is paced (Vp), the STI can be measured from the ventricular pacing (Vp) signal to the end of ventricular ejection such as represented by the onset of S2 heart sound, that is, STI≈Vp−S2 interval.

The DTI represents the duration of total electro-mechanical diastole. The DTI spans from the closure of the aortic valve to the onset of the atrial depolarization in the next cardiac cycle. In an example, the DTI can be measured as the interval from the S2 heart sound to the onset of the QRS complex on the ECG or the atrial activation event in an intracardiac EGM of the next cardiac cycle, that is, DTI≈S2−Q interval. Therefore, a STI and the following DTI span the cardiac cycle, that is, CL=STI+DTI. During AF, ventricular filing time can be reduced due to the fast atrial and ventricular contractions, which can result in shortened DTI, thereby deterioration of hemodynamic status. A therapy that leads to elongation of DTI therefore can indicate more effective mitigation of the adverse hemodynamic outcome AF.

The CTI can also include composite measures using two or more of the STI, the DTI, the PEP, the cardiac cycle (CL), or the LVET. Examples of the composite measures can include PEP/LVET ratio, STI/DTI ratio, STI/CL ratio, or DTI/CL ratio, among others. The irregular ventricular activity during AF can also lead increased variability of one or more of CTI measures. For example, the inappropriately irregular ventricular electrical excitation and mechanical contraction during AF can result in fluctuation in diastolic filing time, i.e., the DTI. The increased variability of DTI can further lead to widely varying stroke volume, thereby deteriorating patient's hemodynamic stability. As such, the variability of cardiac timing interval (CTIvar), such as the variability of STI, the variability of the DTI, or the variability of the PEP, can be indicative of the cardiac hemodynamics. The variability can be computed as a range, a variance, a standard deviation, or other measures of spreadness determined from a plurality of measurements of CTI.

Figure 4:
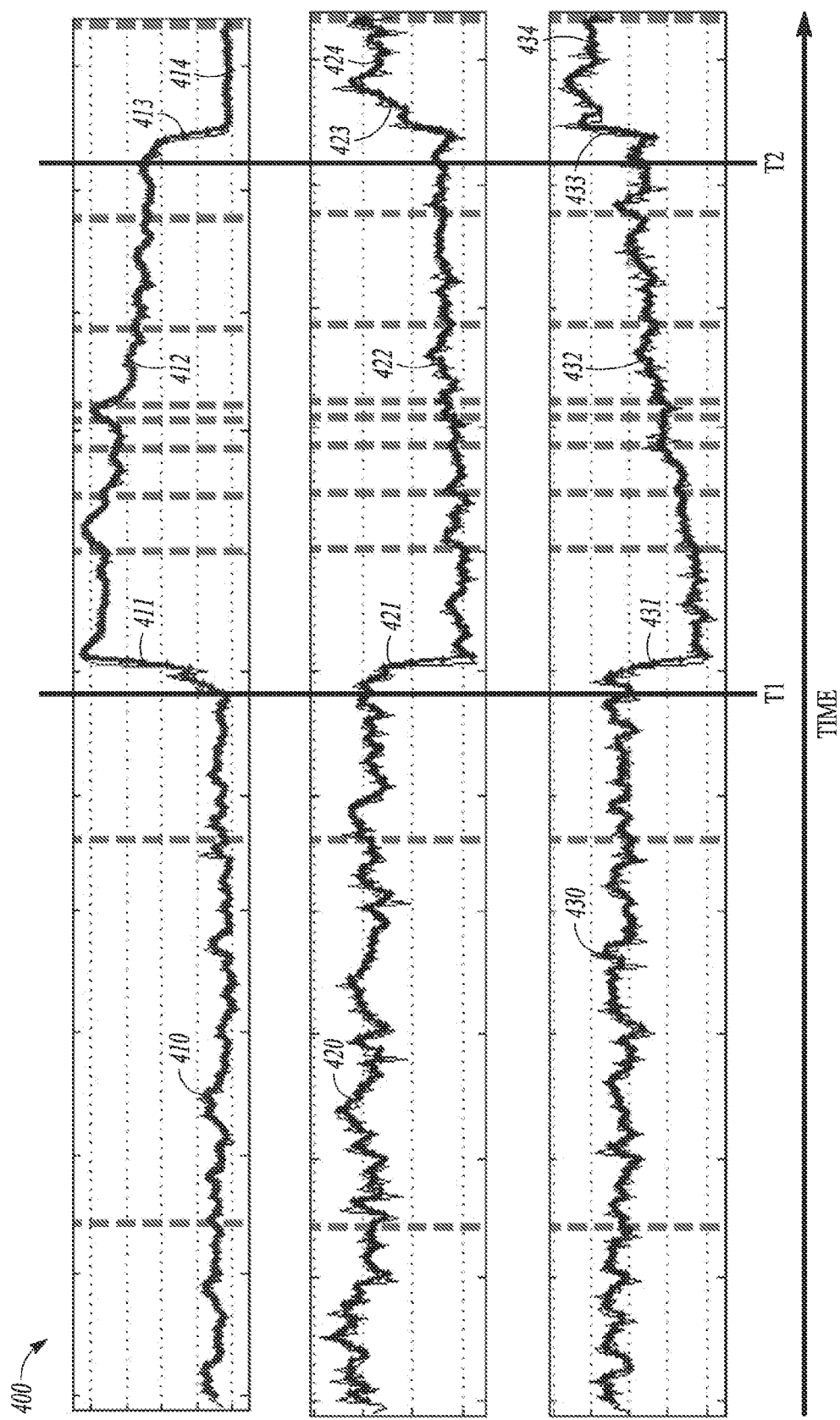
FIG. 4 illustrates an example of changes in heart rate and hemodynamic parameters during the onset and termination of an AF episode.

FIG. 4 illustrates an example 400 of changes in heart rate (HR) and hemodynamic parameters during the onset and termination of an AF episode in a patient. The daily average HR trend signal 410 represents temporal variation of the daily average HR signal over approximately 12 months. Drawn on the same time scale are a daily average S1 heart sound intensity (‖S1‖) trend signal 420 and a daily average S2 heart sound intensity (‖S2‖) trend signal 430. Signals 420 and 430 can be generated by the hemodynamic sensor circuit 230. The intensity of S1 and S2 are each computed as the signal power of S1 or S2 over respective time window.

As illustrated in FIG. 4, in response to an AF onset event occurring at time instant T1, the heart rate increases at 411, the ‖S1‖ decreases at 421 and the ‖S2‖ decreases at 431. During the sustained AF episode (between T1 and T2), the HR signal 412 remains at an elevated level and gradually decreases. Both the ‖S1‖ and ‖S2‖ signals remain lower than their respective pre-AF level, but gradually recover during the AF episode. At time instant T2, an AF termination event occurs. In response to the AF termination event, the heart rate decreases at 413, the ‖S1‖ increases at 423, and ‖S2‖ increases at 433. Following the transitional phases of AF termination, the HR signal 414, the ‖S1‖ signal 424, and the ‖S2‖ signal 434 reach or exceed their respective pre-AF level.

Figure 5:
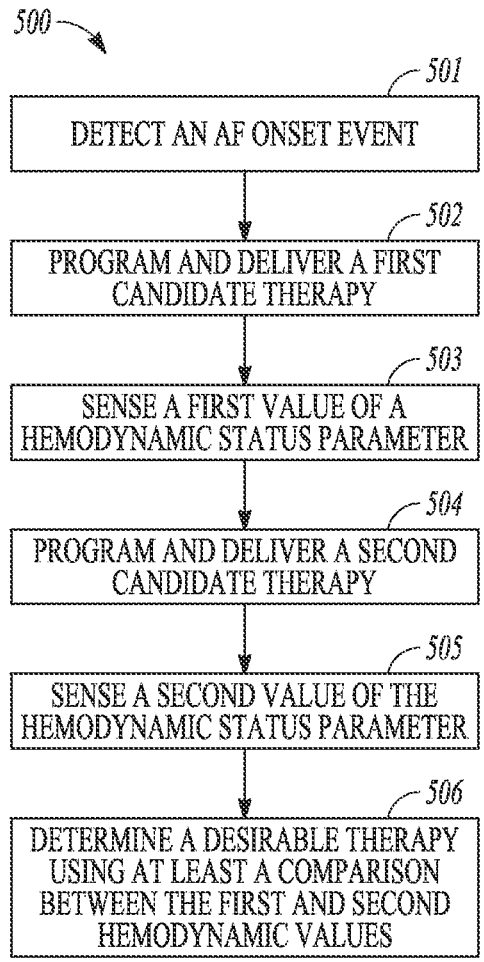
FIG. 5 illustrates an example of a method for determining a desired therapy for treating AF.

FIG. 5 illustrates an example of a method 500 for determining a desired therapy for treating atrial tachyarrhythmia such as atrial fibrillation (AF) in a patient. The method 500 can be implemented and operate in an ambulatory medical device or in a remote patient management system. In an example, the method 500 can be performed by the hemodynamic sensor-based AF therapy determination circuit 113 implemented in the IMD 110, or the external device 120 which can be in communication with the IMD 110.

At 501, an AF onset event can be detected such as by using a system comprising the AF detection circuit 210. A physiologic signal indicative of an AF episode can be sensed using one or more physiologic sensors. In an example, the AF onset event can be sensed using electrocardiograms (ECGs) such as sensed by using electrodes non-invasively attached to a patient's body surface, subcutaneous ECGs such as sensed by using subcutaneously placed electrodes, or intracardiac electrograms (EGMs) such as sensed by using electrodes on one or more of the leads 108A-C or the can 112. In an example, atrial rate can be determined by counting the number of P waves detected from an ECG signal or the number of atrial sensed events detected from an intracardiac EGM sensed at or near an atrium. An AF onset event can be detected when the atrial rate exceeds a specified atrial rate threshold. In another example, ventricular rate and ventricular rate variability cat be determined using R waves or QRS complexes detected from an ECG signal or ventricular sensed events detected from an intracardiac EGM sensed at or near a ventricle. An AF onset event can be detected when the ventricular rate exceeds a specified ventricular rate threshold and the variability of the ventricular rate exceeds a specified variability threshold. Additionally or alternatively, a cardiac mechanical activity signal can be sensed using a physiologic signal such as pressure signal, impedance signal, or heart sound signal. A pulse rate and a variability of the pulse rate can be determined from the cardiac mechanical activity signal. An AF onset event can be detected if the pulse rate exceeds a specified pulse rate threshold and the variability of the pulse rate exceeds a specified variability threshold.

At 502, a first candidate therapy can be programmed and delivered to the patient in response to the detection of the AF onset event. The first candidate therapy can include one or a combination of a cardiac pacing therapy, a neurostimulation therapy, a cardiac ablation therapy, a denervation therapy, or a pharmacological therapy. One example of the cardiac stimulation therapy is ventricular fallback pacing therapy, where the ventricular pacing rate, in response to the detection of AF event, gradually changes to a specified lower rate limit (LRL), and maintains at the rate of LRL until an AF termination event is detected or when a ventricular fallback pacing is terminated. Other examples of cardiac stimulation therapy can include ventricular rate regularization pacing therapy, atrial anti-tachycardia pacing therapy, atrial cardioversion therapy, or atrial defibrillation therapy, among others.

The first candidate therapy can include other therapy modalities that involve different procedure, energy type, or active agents used in the therapy. Programming of the first candidate therapy can include determining therapy parameters associated with therapy strength, dosage, duration, or other parameters associated with therapy generation or configuration of the therapy delivery, such as selection of electrodes for delivering the therapy to a target tissue. For example, programming of an electrostimulation therapy can include selecting parameters of pulse amplitude, pulse waveform, pulse frequency, pulse width, duty cycle, duration, or any other parameters associated with the electrostimulation.

At 503, a first value of a hemodynamic status parameter can be sensed in response to or during the delivery of the first candidate therapy, such as by using a hemodynamic sensor coupled to the hemodynamic sensor circuit 230. The value of the hemodynamic status parameter measured during the delivery of a candidate therapy can indicate effect of the delivered therapy in mitigating the adverse hemodynamic impact caused by the AF episode (e.g., reduced cardiac output or deteriorated hemodynamic status), thereby suggestive of efficacy of the candidate therapy. Examples of the hemodynamic sensor can include pressure sensors configured for sensing arterial pressure, pulmonary artery pressure, left atrial pressure, RV pressure, LV coronary pressure; impedance sensors configured for sensing thoracic impedance or cardiac impedance; temperature sensor configured for sensing blood temperature; accelerometers or microphones configured for sensing one or more heart sounds; optical sensors such as pulse oximeters configured for sensing blood oxygen saturation; chemical sensors configured for sensing central venous pH value. The hemodynamic parameters extracted from the hemodynamic signals can include a statistical index derived from the plurality of measurements of the physiologic variables, such as mean, median or other central tendency measures, or second order statistics including variance or standard deviation of the measurements, a histogram of the hemodynamic parameter intensity, or higher order statistics of the measurements. Alternatively or additionally, the hemodynamic parameter generator circuit 231 can generate a hemodynamic parameter using one or more signal trends of the physiologic parameter (such as intensity of the physiologic parameter over time), one or more signal morphological descriptors, or signal power spectral density at a specified frequency range.

At 504, a second candidate therapy can be programmed and delivered to the patient in response to the detection of the AF onset event. Similar to the programming of the first candidate therapy, the second candidate therapy can include one or a combination of a cardiac pacing therapy, a neurostimulation therapy, a cardiac ablation therapy, a denervation therapy, or a pharmacological therapy. In one example, the second candidate therapy can be of a different therapy modality than the first candidate therapy. For example, the first candidate therapy can be a cardiac pacing therapy, and the second candidate therapy can be a vagus nerve stimulation therapy. In another example, the first candidate therapy can be a ventricular rate regularization pacing therapy, and the second candidate therapy can be an atrial antitachycardia pacing therapy.

The second candidate therapy can be of the same therapy modality as the first candidate therapy, but has at least one therapy parameter different than that of the first candidate therapy. In an example, the first candidate therapy is a ventricular fallback pacing therapy where the pacing rate gradually changes to a first LRL while the second candidate therapy is a ventricular fallback pacing therapy where the pacing rate gradually changes to a second LRL value different from the first LRL value.

In some examples, a specified post therapy recovery period can be administered after the cessation of the first therapy and before the initiation of the second therapy. A recovery period may allow the patient's hemodynamic status to reach a baseline level comparable to that before the first candidate therapy, thereby alleviating any residual hemodynamic impact exerted by the first therapy. It would also yield more reliable comparison between the hemodynamic status parameter in response to or during the first candidate therapy and the hemodynamic status parameter in response to or during the second candidate therapy.

At 505, a second value of a hemodynamic status parameter can be sensed in response to or during the delivery of the second candidate therapy. The hemodynamic status parameter sensed at 505 can be of the same type as the hemodynamic status parameter sensed at 503. At 506, a desirable therapy can be determined using the first value of the hemodynamic status parameter and the second value of the hemodynamic status parameter. In an example, the desirable therapy can be selected as the candidate therapy that yields higher value of the hemodynamic parameter. In another example, the desirable therapy can be selected as the candidate therapy that results in faster hemodynamic recovery in response to or during candidate therapy delivery.

The selection of desirable therapy between the first and second candidate therapies as discussed in the method 500 can be slightly modified and extend to therapy selection from more than two candidate therapies. For example, the method 500 can include individually programming three or more candidate therapies with non-identical therapy modalities or non-identical therapy parameters, sequentially delivering each candidate therapy to the patient, and sensing the hemodynamic status parameters in response to or during each of the delivered candidate therapy, and determining from the three or more candidate therapies at least one desirable therapy based on the comparison of the hemodynamic status parameters.

Figure 6:
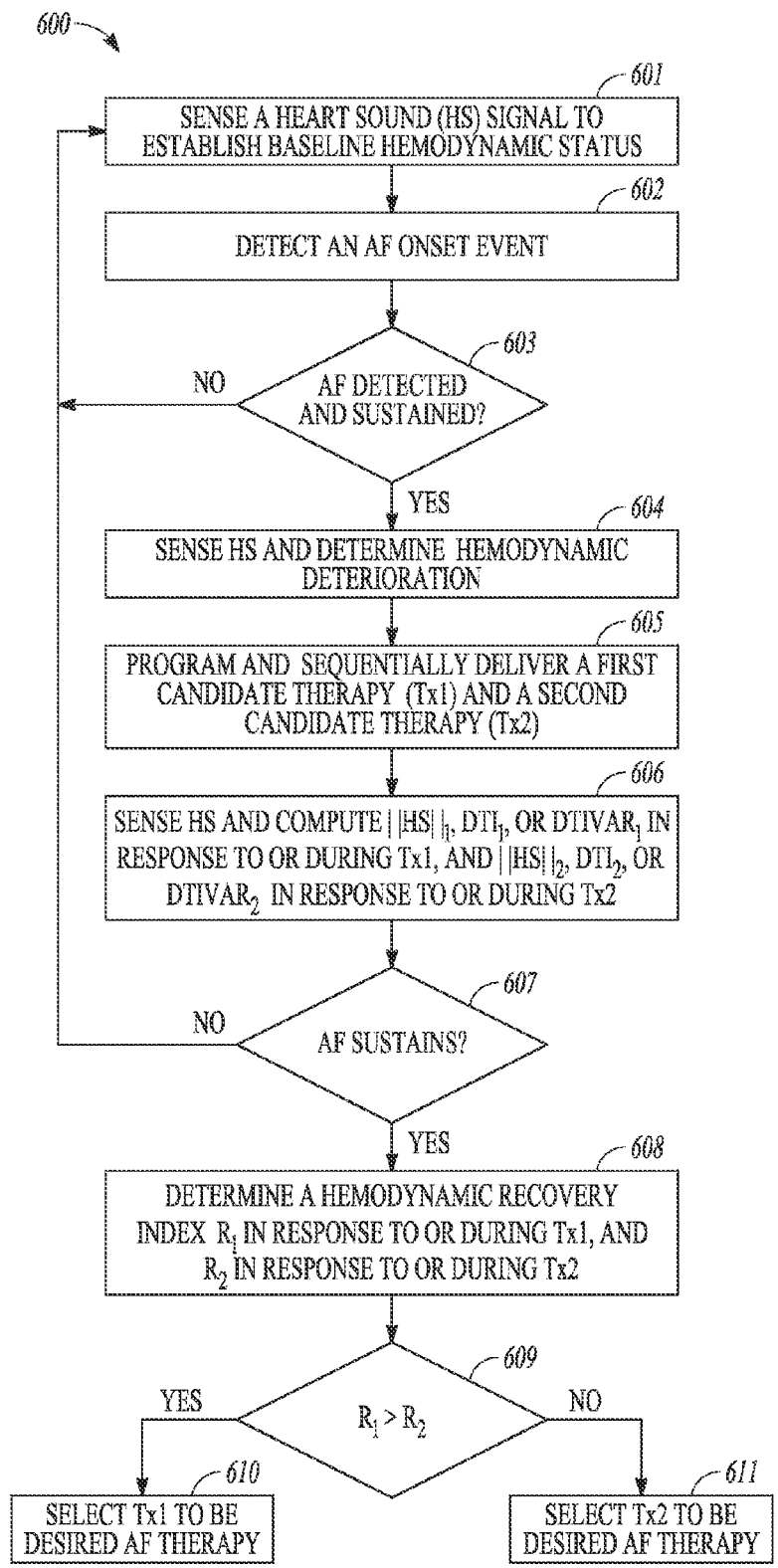
FIG. 6 illustrates an example of a method for determining a desired therapy for treating AF using heart sound sensors.

FIG. 6 illustrates an example of a method 600 for determining a desired therapy for treating atrial tachyarrhythmia such as atrial fibrillation (AF) in a patient using heart sound sensors. The method 600 can be an embodiment of the method 500. In an example, the method 600 can be performed by the hemodynamic sensor-based AF therapy determination circuit 113.

The method 600 starts at a process of sensing a heart sound (HS) signal from a patient. The HS signal can be sensed by using a heart sound sensor such as an ambulatory accelerometer or an ambulatory microphone. The HS signal can be processed such as by using the HS component detector circuit 320, including amplification, digitization, filtering, or other signal conditioning operations. In an example, the HS signal can be filtered to a frequency range of approximately between 5 and 90 Hz. In another example, the HS signal can be filtered to a frequency range between 9 and 90 Hz. From the HS signal, one or more HS components such as S1, S2, S3 or S4 heart sounds can be detected such by using respective HS detection windows. A HS-based hemodynamic parameter, such as HS intensity or a timing interval measured using one or more of the HS components, can be calculated to establish a baseline hemodynamic status of the patient.

At 602, an AF onset event is detected. Similar to the process 501 of the method 500, the AF onset event detection can involve sensing a cardiac electrical signal such as an ECG or an intracardiac EGM, and detecting an AF onset event if the atrial rate exceeds a specified threshold, or if the ventricular rate and ventricular rate variability exceeds their respectively specified threshold. If no AF onset event is detected or the AF event does not sustain for a specified minimal duration at 603, a therapy is deemed not warranted, and HS signal monitor and baseline hemodynamic status evaluation can be continued at 601. However, if an AF onset event is detected and sustains for a specified duration, the HS signal can be measured during the AF event at 604, and a level of hemodynamic deterioration can be determined using the HS signal. For example, a relative change of the hemodynamic status from the baseline hemodynamic status to the hemodynamic parameters obtained during the detected AF event can be computed. Such a relative change can be indicative of an impact of AF event on hemodynamic deterioration.

At 605, a first candidate therapy (Tx1) and a second candidate therapy (Tx2) can be individually programmed, and sequentially delivered to the patient. The programming of Tx1 and Tx2 can be based on the detected hemodynamic deterioration as provided at 604. For example, the first and second candidate therapies can be programmed with one or more of higher dosage, longer duration, or stronger therapy strength if more significant hemodynamic deterioration is detected during the AF event.

Similar to the discussion with reference to processes 502 and 504 in FIG. 5, Tx1 and Tx2 can respectively include one or a combination of a cardiac pacing therapy, a neurostimulation therapy, a cardiac ablation therapy, a denervation therapy, or a pharmacological therapy. Examples of cardiac stimulation therapy can include one or more of ventricular fallback pacing therapy, ventricular rate regularization pacing therapy, atrial anti-tachycardia pacing therapy, atrial cardioversion therapy, or atrial defibrillation therapy, among others. The second candidate therapy can be of different therapy modality than the first candidate therapy. The second candidate therapy can also be of the same therapy modality as the first candidate therapy, but has at least one therapy parameter different than that of the first candidate therapy. The therapy parameter can be associated with therapy strength, dosage, duration, stimulation site, or other configuration parameter.

At 606, the HS signal can be measured during the Tx1 and Tx2, and one or more of HS features, including HS intensity ($\|HS\|$), a cardiac timing interval (CTI) such as a diastolic timing interval (DTI), or variability of the CTI such as variability of the DTI (DTIvar) can be calculated. The $\|HS\|$ can include intensity of an S1 heart sound ($\|S1\|$) or intensity of S2 heart sound ($\|S2\|$). Examples of the intensity of a HS component can include amplitude of a detected HS component in a time-domain HS signal, a transformed HS signal such as integrated HS energy signal, or in a frequency-domain HS signal such as the peak value of the power spectral density. The CTI represents the timing interval between two cardiac events such as a cardiac electrical event detected from the cardiac electrical signal and a mechanical event such as detected from a cardiac mechanical signal or a hemodynamic signal such as heart sound signal. The CTI can include a systolic timing interval (STI), a diastolic timing interval (DTI), a pre-ejection period (PEP), among others. The CTI can also include composite measures among STI, DTI, PEP, cardiac cycle (CL), or left ventricular ejection time (LVET). Examples of the composite measures can include PEP/LVET ratio, STI/DTI ratio, STI/CL ratio, or DTI/CL ratio, among others. The variability can be computed as a range, a variance, a standard deviation, or other measures of spreadness determined from a plurality of measurements of CTI.

At 607, the sustainability of AF event is assessed. If AF no long sustains, the therapy is deemed not warranted, and HS signal monitor and baseline hemodynamic status evaluation can be continued at 601. However, if AF sustains, at 608, a hemodynamic recovery index $R_1$ in response to or during Tx1 can be determined using one or more of the $\|HS\|_1$, $DTI_1$ and $DTIvar_1$. Similarly, a hemodynamic recovery index $R_2$ in response to or during Tx2 can be determined using one or more of the $\|HS\|_2$, $DTI_2$ and $DTIvar_2$. $R_1$ and $R_2$ are indicative of patient's hemodynamic status in response to or during respective candidate AF therapies Tx1 and Tx2.

The hemodynamic recovery index $R_1$ or $R_2$ can be proportional to $\|HS\|$, such that Tx1 can be selected to be the desirable therapy if the $\|HS\|_1$ is greater than the $\|HS\|_2$, or Tx2 is selected to be the desirable therapy if $\|HS\|_2$ is greater than the $\|HS\|_1$. The hemodynamic recovery index $R_1$ or $R_2$ can also be proportional to DTI, such that Tx1 can be selected to be the desirable therapy if the $DTI_1$ is greater than the $DTI_2$, or Tx2 can be selected to be the desirable therapy if the $DTI_2$ is greater than the $DTI_1$. In another example, the hemodynamic recovery index $R_1$ or $R_2$ can be inversely proportional to DTIvar, such that Tx1 can be selected to be the desirable therapy if the $DTIvar_1$ is smaller than the $DTIvar_2$, or Tx2 can be selected to be the desirable therapy if the $DTIvar_2$ is smaller than the $DTIvar_1$.

The hemodynamic recovery index $R_1$ can be a composite index computed as a linear or nonlinear combination of $\|HS\|_1$, $DTI_1$ and $DTIvar_1$, and $R_2$ can be computed as a linear or nonlinear combination of $\|HS\|_2$, $DTI_2$ and $DTIvar_2$. In an example, $R_1$ can be computed as a weighted sum of $\|HS\|_1$, $DTI_1$ and $DTIvar_1$, e.g., $R_1 = a_1 \cdot \|HS\|_1 + b_1 \cdot DTI_1 + c_1 \cdot DTIvar_1$, and $R_2$ can be computed as a weighted sum of $\|HS\|_2$, $DTI_2$ and $DTIvar_2$, e.g., $R_2 = a_2 \cdot \|HS\|_2 + b_2 \cdot DTI_2 + c_2 \cdot DTIvar_2$, where $a_1$, $b_1$, $c_1$ and $a_2$, $b_2$, $c_2$ are specified weight factors. In an example, $a_1$ and $a_2$ are positive weight factors such that a stronger HS intensity during the candidate therapy leads to a larger hemodynamic recover index (R value), which suggests more substantial hemodynamic recovery. In another example, $b_1$ and $b_2$ are positive weight factors such that a longer DTI during the delivery of candidate therapy can result in larger hemodynamic recovery index (R value). In another example, $c_1$ and $c_2$ are negative weight factors such that a smaller DTIvar (i.e., less variable diastolic timing interval) during the delivery of candidate therapy leads to greater hemodynamic recovery index (R value), which indicates more significant hemodynamic recovery due to the candidate therapy.

At 609, a comparison between the hemodynamic recovery indices $R_1$ and $R_2$ are performed, if $R_1$ is greater than $R_2$, more significant hemodynamic recovery is detected during Tx1, suggesting Tx1 is more effective than Tx2 in mitigating the adverse hemodynamic outcome caused by the AF event.

Tx1 can therefore be selected as the desired therapy at 610. Conversely, if $R_2$ is greater than $R_1$, more significant hemodynamic recovery is detected during Tx2, suggesting Tx2 is more effective that Tx1 in mitigating the adverse hemodynamic outcome caused by AF; and Tx2 can then be selected as the desired therapy at 611.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc, are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract Is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the fall scope of equivalents to which such claims are entitled.

What is claimed is:

1. A medical system, comprising:
   an atrial fibrillation (AF) detection circuit configured to receive a signal indicative of atrial activity of a patient, and to detect an AF event using the received signal indicative of atrial activity;
   one or more programmable therapy circuits configured to generate and deliver to the patient a respective therapy for treating AF in response to the detection of the AF event;
   a hemodynamic sensor circuit configured to sense a hemodynamic status output indicative of a hemodynamic status of the patient; and
   a therapy selection circuit coupled to the hemodynamic sensor circuit and the one or more programmable therapy circuits, the therapy selection circuit configured to:
   in response to the detection of the AF event, control the one or more programmable therapy circuits to generate and sequentially deliver to the patient a first candidate therapy and a different second candidate therapy;
   receive from the hemodynamic sensor circuit a first value of the hemodynamic status output in response to or during the delivery of the first candidate therapy and a second value of the hemodynamic status output in response to or during the delivery of the second candidate therapy; and
   select a desired therapy based on the first and second values of the hemodynamic status output.

2. The system of claim 1, wherein:
   the one or more programmable therapy circuits are configured to generate and deliver to the patient one or more of a cardiac stimulation therapy, a cardiac ablation therapy, a neurostimulation therapy, a denervation therapy, or a pharmacological therapy; and
   the therapy selection circuit is configured to control the one or more programmable therapy circuits to respectively generate and sequentially deliver to the patient the first and second candidate therapies each selected from the one or more of the cardiac stimulation therapy, the cardiac ablation therapy, the neurostimulation therapy, the denervation therapy, or the pharmacological therapy.

3. The system of claim 2, wherein the cardiac stimulation therapies include one or more of ventricular fallback pacing therapy, ventricular rate regularization pacing therapy, atrial anti-tachycardia pacing therapy, atrial cardioversion therapy, or atrial defibrillation therapy.

4. The system of claim 1, wherein the second candidate therapy differs from the first candidate therapy by at least one therapy parameter associated with therapy generation or configuration, the at least one therapy parameter including a therapy dosage, a therapy duration, or a therapy strength.

5. The system of claim 1, wherein the hemodynamic sensor circuit includes:
- a heart sound sensor configured to sense a heart sound (HS) signal; and
- a hemodynamic parameter generator circuit configured to detect, using the HS signal, one or more HS components including an S1, an S2, or an S3 heart sound.

6. The system of claim 5, wherein:
- the hemodynamic parameter generator circuit is configured to determine a HS strength indicative of strength of the HS component including strength of the S1, the S2, or the S3 heart sound; and
- the therapy selection circuit is configured to receive, from the hemodynamic parameter generator circuit, a first value of the HS strength in response to or during the delivery of the first candidate therapy and a second value of the HS strength in response to or during the delivery of the second candidate therapy, and to select the first candidate therapy as the desired therapy if the first value of the HS strength is greater than the second value of the HS strength, or select the second candidate therapy as the desired therapy if the second value of the HS strength is greater than the first value of the HS strength.

7. The system of claim 5, further comprising a cardiac activity sensor configured to sense a cardiac electrical activity including atrial depolarization or ventricular depolarization, wherein:
- the hemodynamic parameter generator circuit is configured to determine a diastolic timing interval (DTI) using the sensed cardiac electrical activity and the detected HS component; and
- the therapy selection circuit is configured to receive, from the hemodynamic parameter generator circuit, a first value of DTI in response to or during the delivery of the first candidate therapy and a second value of DTI in response to or during the delivery of the second candidate therapy, and to select the first candidate therapy as the desired therapy if the first value of DTI is greater than the second value of DTI, or select the second candidate therapy as the desired therapy if the second value of DTI is greater than the first value of DTI.

8. The system of claim 5, further comprising a cardiac activity sensor configured to sense a cardiac electrical activity including atrial depolarization or ventricular depolarization, wherein the hemodynamic parameter generator circuit is configured to determine a variability of cardiac timing interval (CTIvar) using the sensed cardiac electrical activity and the detected HS component.

9. The system of claim 8, wherein:
- the hemodynamic parameter generator circuit is configured to sense the CTIvar including a variability of diastolic timing interval (DTIvar); and
- the therapy selection circuit is configured to receive, from the hemodynamic parameter generator circuit, a first value of DTIvar in response to or during the delivery of the first candidate therapy and a second value of DTIvar in response to or during the delivery of the second candidate therapy, and to select the first candidate therapy as the desired therapy if the first value of DTIvar is lower than the second value of DTIvar, or select the second candidate therapy as the desired therapy if the second value of DTIvar is lower than the first value of DTIvar.

10. The system of claim 1, wherein the therapy selection circuit is configured to, prior to the delivery of the first and second candidate therapies:
- receive from the hemodynamic sensor circuit a pre-therapy hemodynamic status output and determine a level of hemodynamic deterioration including a relative change of hemodynamic status in response to the detected AF event; and
- control the one or more programmable therapy circuits to generate respectively the first and second candidate therapies based on the level of hemodynamic deterioration.

11. A medical system, comprising:
- a hemodynamic sensor circuit configured to sense a hemodynamic status output indicative of a hemodynamic status of a patient;
- an atrial fibrillation (AF) detector configured to receive a signal indicative of atrial activity of a patient, and to detect an AF onset event from the received signal indicative of atrial activity;
- one or more programmable therapy circuits configured to generate and deliver to the patient a respective therapy for treating AF in response to the detection of the AF onset event; and
- a therapy selection circuit coupled to the hemodynamic sensor circuit and the one or more programmable therapy circuits, the therapy selection circuit configured to:
  - in response to the detection of the AF event, control the one or more programmable therapy circuits to generate and sequentially deliver to the patient a first candidate therapy and a different second candidate therapy;
  - receive from the hemodynamic sensor circuit a first value of pre-therapy hemodynamic status output before the delivery of the first candidate therapy and a first value of the hemodynamic status output in response to or during the delivery of the first candidate therapy;
  - receive from the hemodynamic sensor circuit a second value of pre-therapy hemodynamic status output before the delivery of the second candidate therapy and a second value of the hemodynamic status output in response to or during the delivery of the second candidate therapy;
  - calculate a first relative change from the first pre-therapy hemodynamic status output to the first value of the hemodynamic status output, and a second relative change from the second pre-therapy hemodynamic status output to the second value of the hemodynamic status output; and
  - select the first candidate therapy as a desired therapy if the first relative change is greater than the second relative change, or select the second candidate therapy as the desired therapy if the second relative change is greater than the first relative change.

12. A method for operating a medical system to treat an atrial fibrillation (AF) in a patient, comprising:
- receiving a signal indicative of atrial activity of the patient and detecting an AF onset event from the received signal indicative of atrial activity;
- in response to the detected AF onset event, delivering to the patient a first candidate therapy for treating AF via the medical system;
- sensing a first value of a hemodynamic status parameter from the patient in response to or during the delivery of the first candidate therapy;

in response to the detected AF onset event, delivering to the patient a second candidate therapy for treating AF different from the first candidate therapy via the medical system;

sensing a second value of the hemodynamic status parameter from the patient in response to or during the delivery of the second candidate therapy; and determining a desired therapy, via the medical system, based on the first and second values of the hemodynamic status output.

13. The method of claim 12, wherein the first and second candidate therapies are each selected from one or more of a cardiac stimulation therapy, a cardiac ablation therapy, a neurostimulation therapy, a denervation therapy, or a pharmacological therapy.

14. The method of claim 13, wherein the cardiac stimulation therapies include one or more of ventricular fallback pacing therapy, ventricular rate regularization pacing therapy, atrial anti-tachycardia pacing therapy, atrial cardioversion therapy, or atrial defibrillation therapy.

15. The method of claim 12, wherein the second candidate therapy differs from the first candidate therapy by at least one therapy parameter associated with therapy generation or configuration, the at least one therapy parameter including a therapy dosage, a therapy duration, or a therapy strength.

16. The method of claim 12, wherein the hemodynamic status parameter includes a heart sound (HS) strength indicative of strength of an S1, an S2, or an S3 heart sound, and wherein:

sensing the first value of a hemodynamic status parameter includes sensing a first value of the HS strength in response to or during the delivery of the first candidate therapy;

sensing a second value of the hemodynamic status parameter includes sensing a second value of the HS strength in response to or during the delivery of the second candidate therapy; and selecting a desired therapy includes selecting the first candidate therapy as the desired therapy if the first value of the HS strength is greater than the second value of the HS strength, or selecting the second candidate therapy as the desired therapy if the second value of the HS strength is greater than the first value of the HS strength.

17. The method of claim 12, comprising sensing a cardiac electrical activity including atrial depolarization or ventricular depolarization and sensing a HS component including an S1, an S2, or an S3 heart sound, the hemodynamic status parameter including a diastolic timing interval (DTI) determined using the sensed cardiac electrical activity and the sensed HS component, wherein:

sensing the first value of a hemodynamic status parameter includes sensing a first value of the DTI in response to or during the delivery of the first candidate therapy;

sensing the first value of a hemodynamic status parameter includes sensing a second value of the DTI in response to or during the delivery of the second candidate therapy; and selecting a desired therapy includes selecting the first candidate therapy as the desired therapy if the first value of the DTI is greater than the second value of the DTI, or selecting the second candidate therapy as the desired therapy if the second value of the DTI is greater than the first value of the DTI.

18. The method of claim 12, comprising sensing a cardiac electrical activity including atrial depolarization or ventricular depolarization and sensing a HS component including an S1, and S2, or an S3 heart sound, the hemodynamic status parameter including a variability of cardiac timing interval (CTIvar) determined using the sensed cardiac electrical activity and the sensed HS component.

19. The method of claim 18, wherein:

the CTIvar includes a variability of diastolic timing interval (DTIvar);

sensing the first value of a hemodynamic status parameter includes sensing a first value of DTIvar in response to or during the delivery of the first candidate therapy;

sensing the second value of a hemodynamic status parameter includes sensing a second value of DTIvar in response to or during the delivery of the second candidate therapy; and selecting a desired therapy includes selecting the first candidate therapy as the desired therapy if the first value of DTIvar is lower than the second value of DTIvar, or select the second candidate therapy as the desired therapy if the second value of DTIvar is lower than the first value of DTIvar.

20. The method of claim 12, further comprising sensing a pre-therapy hemodynamic status output and determining a level of hemodynamic deterioration before the delivery of the first and second candidate therapies, wherein the first and second candidate therapies are delivered based on the level of hemodynamic deterioration.

* * * * *